United States Patent
Ko et al.

(10) Patent No.: US 8,470,379 B2
(45) Date of Patent: Jun. 25, 2013

(54) **USE OF A POTENT PRODUCT EXTRACTED FROM RHIZOMES OF ZINGIBER OFFICINALE IN TREATING A DISEASE ASSOCIATED WITH *HELICOBACTER PYLORI***

(75) Inventors: Feng-Nien Ko, Taipei (TW); Mo-Chi Cheng, Taipei (TW); Cheng-Ko Liu, Taipei (TW); Jen-Wei Chen, Taipei (TW); Fen Chen, Taipei (TW); Chao-Chi Yei, Taipei (TW)

(73) Assignee: Medical and Pharmaceutical Industry Technology and Development Center, Taipei Hsien (TW)

( * ) Notice: Subject to any disclaimer, the term of this patent is extended or adjusted under 35 U.S.C. 154(b) by 5 days.

(21) Appl. No.: 12/911,143

(22) Filed: Oct. 25, 2010

(65) Prior Publication Data
US 2011/0038966 A1 Feb. 17, 2011

Related U.S. Application Data

(62) Division of application No. 11/907,854, filed on Oct. 18, 2007, now Pat. No. 7,842,318.

(51) Int. Cl.
*A61K 36/9068* (2006.01)

(52) U.S. Cl.
USPC .......................................... 424/756; 424/773

(58) Field of Classification Search
None
See application file for complete search history.

(56) References Cited

FOREIGN PATENT DOCUMENTS

GB 2366565 3/2002
JP 08119872 5/1996

OTHER PUBLICATIONS

Yoshikawa (Chem. Pharm. Bull. (1994), vol. 42, No. 6, pp. 1226-1230).*

Third-Party Submission Under 37 CFR 1.99 filed in present U.S. Appl. No. 12/911,143 on Mar. 21, 2011 by Council of Scientific & Industrial Research, New Delhi, India, pp. 1-29.
Publication I: Bhavamisra; Bhavaprakasa; Edited and translated by Brahmasankara Misra, Part-II: Chaukhamba Sanskrit Sansthan, Varansai, Edition 7th, 2000, p. 329.
Publication II: Samgadharacarya; Sarngadhara Sarnhita, Translated by Smt. Shailaja Srivastava: Chaukhamba Orientalia, Varanasi, Edition 2nd, 1998, p. 170.
Publication III: Vangasena; Vangasena, Commentator Shaligram Vaisya, Edited Shankar Ialji Jain; Khemraj Shrikrishna Das Prakashan, Bombay, Edition 1996, pp. 426-427.
Publication IV: Govinda Dasa; Bhaisajya Ratnavali, Edited by Rajeshvaradutta Shastri, Translated by Ambikaduttashastri: Chaukhamba Sanskrit Sansthan, Varanasi, Edition 14th, 2001, p. 461.
Publication V: Mohammad Shareef Khan; Ilaaj-Al-Amraaz, Afzal-Al-Matabe, Barqi Press, Delhi, 1921, pp. 177-178.
Publication VI; Mohammad Akbar Arzani; Qaraabaadeen Qaadri, Ahmadi Publication, Delhi, 1968, p. 202.
Publication VII: Kandasamy Mudaliar; Athmarakshaamirtham Pub: Ilakkana Achagam, Chennai, 1879, p. 348.
Publication VIII: Kandasamy Mudaliar; Athmarakshaamirtham Pub: Ilakkana Achagam, Chennai, 1879, p. 345.

* cited by examiner

*Primary Examiner* — Susan Hoffman
(74) *Attorney, Agent, or Firm* — Bacon & Thomas, PLLC

(57) ABSTRACT

A new use of a potent product extracted from rhizomes of *Zingiber officinale* in treating a disease associated with *Helicobacter pylori* such as gastritis, gastric ulcer or duodenal ulcer in a patient. The potent product is prepared by a process including the steps of a) preparing a crude extract from rhizomes of *Zingiber officinale*, said crude extract comprising 6-gingerol and 6-shogaol; b) introducing the crude extract to a normal phase chromatography column, and eluting the column with a first eluent having a polarity lower than that of a mixture of n-hexane and ethyl acetate in a weight ratio of 6:4 to obtain a potent fraction. Preferably, the potent fraction is substantially free of both 6-gingerol and 6-shogaol.

11 Claims, 10 Drawing Sheets

USE OF A POTENT PRODUCT EXTRACTED FROM RHIZOMES OF ZINGIBER OFFICINALE IN TREATING A DISEASE ASSOCIATED WITH *HELICOBACTER PYLORI*

CROSS REFERENCES TO THE RELATED APPLICATIONS

This application is a divisional application of U.S. patent application Ser. No. 11/907,854, filed Oct. 18, 2007 now U.S. Pat. No. 7,842,318, (of which the entire disclosure of the pending, prior application is hereby incorporated by reference).

FIELD OF THE INVENTION

The present invention is related to a new use of a potent product extracted from rhizomes of *Zingiber officinale* in treating a disease associated with *Helicobacter pylori* such as gastritis, gastric ulcer or duodenal ulcer in a patient.

BACKGROUND OF THE INVENTION

Chinese crude drugs or spices eg. *Zingiber officinale, Eugenia caryophyllata, Allium sativum,* have been used in medicine and in flavoring foods. Crude ginger is used as an anti-emetic and expectorant, an anti-tussive and accelerator of the digestive organs. Semi-dried old crude ginger is also used for stomachache, chest pain, low back pain, cough, common cold and as a cure for a form of edema being called "stagnate of water". Zingerone is the major component which accounts for the spicy character of ginger; gingerol and shogaol are other pungent components in ginger. Gingerol has cardio-tonic action, suppresses the contraction of isolated portal veins in mice, and modulates the eicosanoid-induced contraction of mouse and rat blood vessels. Both gingerol and shogaol are mutagenic, whereas zinger and zingerone have been found to exhibit antimutagenic activity. Shogaol has inhibitory activity on the carrageenin-induced paw edema and platelet aggregation [U.S. Pat. No. 5,804,603, Background of the Invention].

U.S. Pat. No. 6,855,347 discloses a composition for treating gastric ulcer and a process for preparing the same, wherein the composition comprising an extract obtained from the plant parts of *Aegle marmetos* and *Withania somnifra* and from the plant parts of at least one member selected from the group consisting of eight plants, wherein one of them is *Zingiber officinale*. The extract of the composition is preferably an aqueous extract.

Japanese patent publication No. 2004-115536 discloses anti-*Helicobacter pyroli* potent product useful for prophylaxis and treatment of gastritis and gastric and duodenal ulcer, which comprises using one or more galenicals selected from Sophorae radix, Anisi stellati Frutus, *Myristica fragrans, Isodon japonicus* Hara, *Swertia japonica, Florence fennel, Zingiber siccatum*, Atractylodes rhizome, ginger, Saussureae radix and gayangae rhizoma.

It is concluded in the study of an article published in *Anticancer Research* 23(5A): 3699-3702, 2003, that ginger root extracts containing the gingerols inhibit the growth of *H. pylori* CagA+ strains.

SUMMARY OF THE INVENTION

An objective of the present invention is to provide a potent product in treating a disease associated with *Helicobacter pylori* which is prepared from rhizomes of *Zingiber officinale*.

Preferably, the potent product prepared in the present invention is significantly more effective in comparison with a crude aqueous extract or a crude organic solvent extract from rhizomes of *Zingiber officinale*.

It is disclosed in the present invention that an aqueous eluate obtained by subjecting the crude organic solvent extract to an elution treatment with a reverse phase chromatography column has the weakest potency in treating said disease, and an eluate of an eluent having a relatively lower polarity has an improved potency. It is surprised to find that an eluate of an eluent having a polarity sufficiently low so that the eluate is free of both 6-gingerol and 6-shogaol has the strongest potency. This finding is advantageous because 6-gingerol and 6-shogaol are pungent components and are relatively less stable chemicals.

Preferred embodiments of the invention include (but not limited to) the following:

1. A method of treating a disease associated with *Helicobacter pylori* in a patient comprising administering to the patient a therapeutically effective amount of a potent product prepared from rhizomes of *Zingiber officinale*, said potent product being prepared by a process comprising the following steps:

a) preparing a crude extract from rhizomes of *Zingiber officinale*, said crude extract comprising 6-gingerol and 6-shogaol;

b) introducing the crude extract to a reverse phase chromatography column or a normal phase chromatography column, and eluting the column with a first eluent and a second eluent in sequence, i) said first eluent having a polarity lower than water and said second eluent having a polarity lower than that of the first eluent when the reverse phase chromatography column is used, or ii) said second eluent having a polarity lower than that of a mixture of ethyl acetate (EA) and methanol in a weight ratio of 1:1 and said first eluent having a polarity lower than that of the second eluent when the normal phase chromatography column is used, so that a first eluate resulting from elution of the first eluent and a second eluate resulting from elution of the second eluent are obtained; and c) removing the first eluent from the first eluate by evaporation, so that a first concentrated eluate is obtained and is able to be used as the potent product or removing the second eluent from the second eluate by evaporation, so that a second concentrated eluate is obtained and is able to be used as the potent product;

wherein step a) comprises steps i) to iv), or comprises step I), step I'), or step I"), wherein said steps i) to iv) are:

i) shedding fresh rhizomes of *Zingiber officinale* and filtering the resulting mixture to obtain a filtrate and a residue;

ii) extracting the filtrate with a first organic solvent, recovering the resulting extraction solution of the first organic solvent, and evaporating the first organic solvent from the extraction solution to obtain a first concentrated extraction solution;

iii) extracting the residue with a second organic solvent, recovering the resulting extraction solution of the second organic solvent, and evaporating the second organic solvent from the extraction solution to obtain a second concentrated extraction solution; and iv) combining the first concentrated extraction solution and the second concentrated extraction solution to obtain the crude extract;

said step I) is:

I) extracting dried rhizomes of *Zingiber officinale* with an organic solvent which is the same as said second organic solvent, recovering the resulting extraction solution of the organic solvent, and evaporating the organic solvent from the extraction solution to obtain the crude extract;

said step I') is:

I') steam distilling dried rhizomes of Zingiber officinale, and concentrating the resulting distillate by evaporation to obtain the crude extract; and said step I") is:

I") extracting powder of dried rhizomes of Zingiber officinale with supercritical $CO_2$, recovering the resulting extraction solution of the supercritical $CO_2$, and evaporating $CO_2$ from the extraction solution to obtain the crude extract.

2. The method according to Item 1, wherein said disease is gastric ulcer.

3. The method according to Item 1, wherein said crude extract is prepared from the method comprising step i) to iv).

4. The method according to Item 3, wherein said first organic solvent is ethyl ether, and said second organic solvent is acetone, methanol, ethanol, a mixture of methanol and water, a mixture of ethanol and water, or a combination of them 5. The method according to Item 4, wherein said second organic solvent is acetone.

6. The method according to Item 1, wherein said crude extract is prepared from the method comprising step I).

7. The method according to Item 6, wherein said organic solvent is acetone, methanol, ethanol, a mixture of methanol and water, a mixture of ethanol and water, or a combination of them.

8. The method according to Item 7, wherein said organic solvent is acetone, ethanol or a mixture of ethanol and water.

9. The method according to Item 1, wherein the reverse phase chromatography column is used, and the first eluent has a polarity lower than that of a mixture of ethanol and water having 40% of ethanol by weight.

10. The method according to Item 9, wherein the first eluent is methanol, a mixture of methanol and water, ethanol, a mixture of ethanol and water, a mixture of acetone and water, or a combination of them.

11. The method according to Item 10, wherein the first eluent is a mixture of ethanol and water.

12. The method according to Item 11, wherein the reverse phase chromatography column is eluted with water prior to the first eluent.

13. The method according to Item 9, wherein said potent product is said first concentrated eluate, and said first concentrated eluate comprises 6-gingerol and 6-shogaol.

14. The method according to Item 1, wherein the reverse phase chromatography column is used, said potent product is said second concentrated eluate, and the first eluent has a polarity lower than that of a mixture of ethanol and water having 40% of ethanol by weight.

15. The method according to Item 14, wherein said second eluent is acetone, a mixture of acetone and water, a mixture of acetone and methanol, a mixture of acetone and ethanol, a mixture of acetone and C4-C6 alkane, C4-C6 alkane, a mixture of C4-C6 alkane and methanol, a mixture of C4-C6 alkane and ethanol, or a combination of them.

16. The method according to Item 15, wherein said second eluent is acetone.

17. The method according to Item 14, wherein said second concentrated eluate is substantially free of 6-gingerol or 6-shogaol.

18. The method according to Item 14, wherein said second concentrated eluate is substantially free of both 6-gingerol and 6-shogaol.

19. The method according to Item 1, wherein the normal phase chromatography column is used, said potent product is said first concentrated eluate, and the first eluent has a polarity lower than that of a mixture of n-hexane and ethyl acetate in a weight ratio of 6:4.

20. The method according to item 19, wherein the first eluent has a polarity close to that of a mixture of n-hexane and ethyl acetate in a weight ratio of 9:1.

21. The method according to Item 20, wherein the first eluent is a mixture of n-hexane and ethyl acetate in a weight ratio of 9:1.

22. The method according to Item 19, wherein said first concentrated eluate is substantially free of 6-gingerol or 6-shogaol.

23. The method according to Item 19, wherein said first concentrated eluate is substantially free of both 6-gingerol and 6-shogaol.

24. The method according to Item 1, wherein the normal phase chromatography column is used, said potent product is said second concentrated eluate, the second eluent has a polarity close to that of a mixture of n-hexane and ethyl acetate in a weight ratio of 6:4, and said second concentrated eluate comprises 6-gingerol and 6-shogaol.

25. The method according to Item 24, wherein said second eluent is a mixture of n-hexane and ethyl acetate in a weight ratio of 6:4.

The potent product is preferably administered orally.

DETAILED DESCRIPTION OF THE INVENTION

Figure 1:
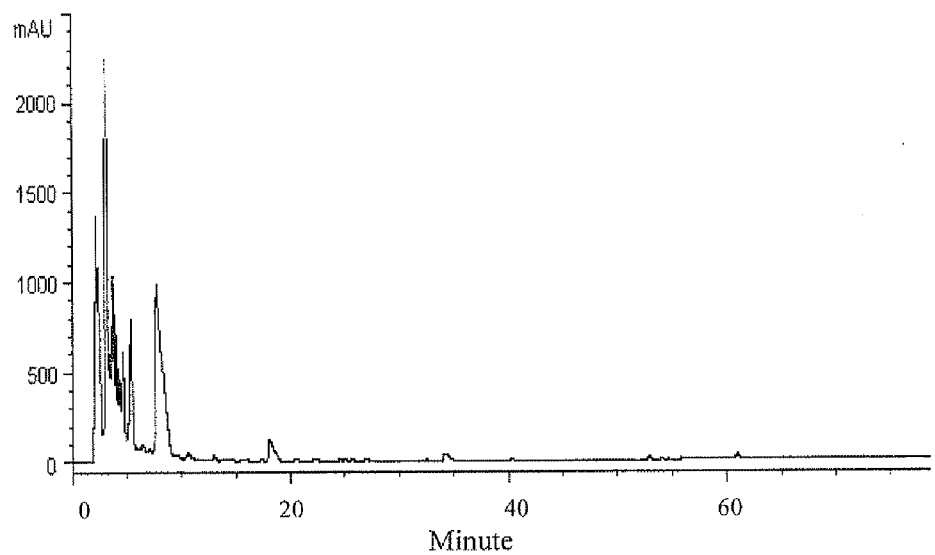
FIG. 1 to FIG. 20 are the results of HPLC analysis of Sample 1 to Sample 20 prepared in the present application.
Figure 2:
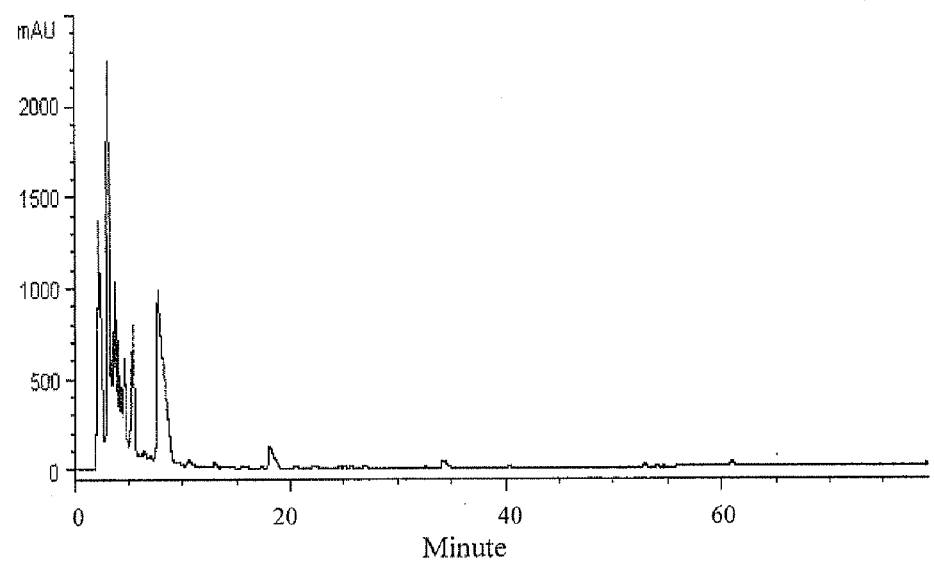
Figure 3:
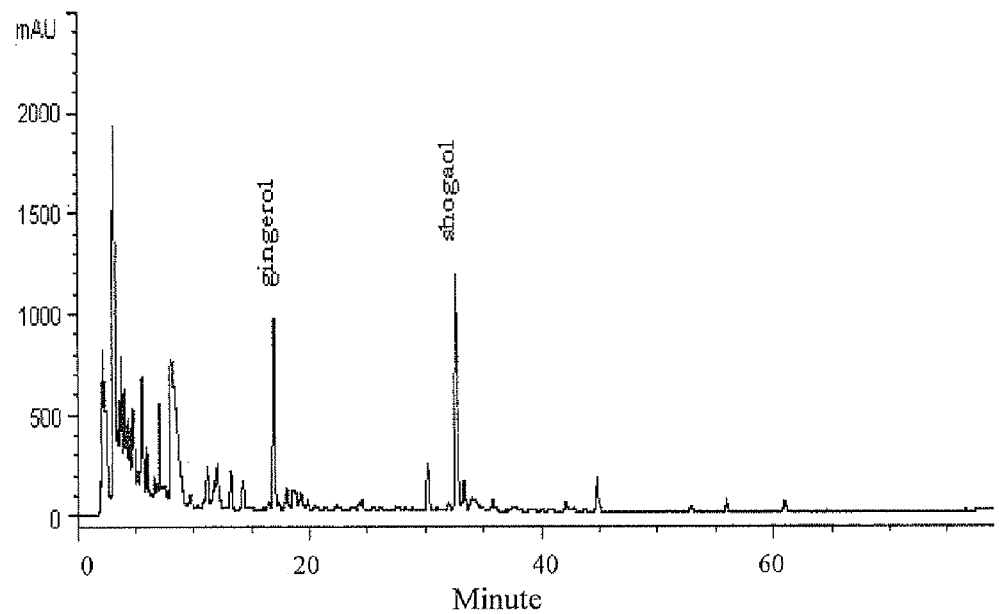
Figure 4:
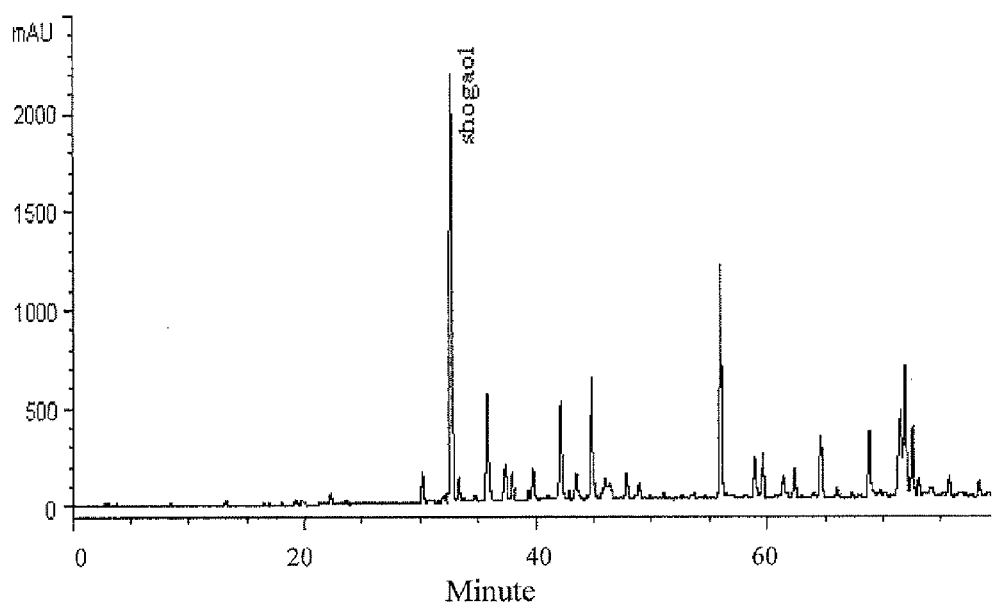
Figure 5:
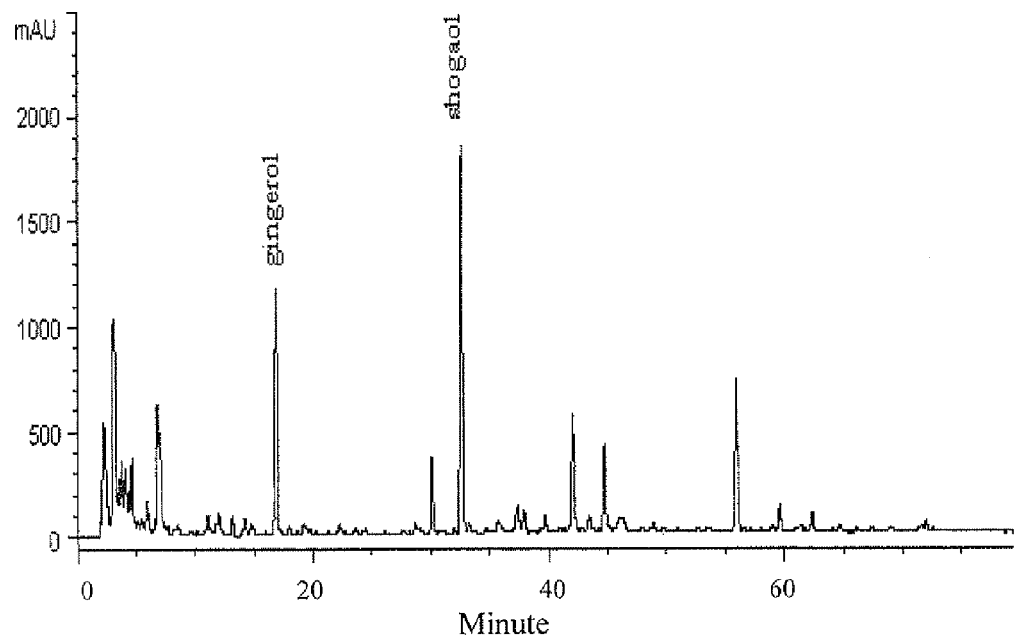
Figure 6:
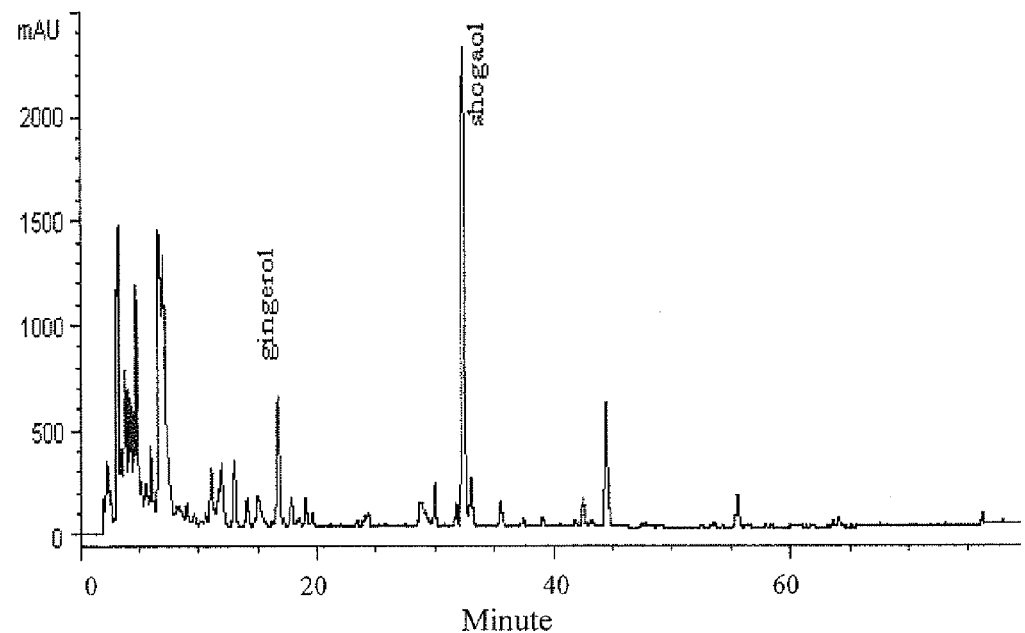
Figure 7:
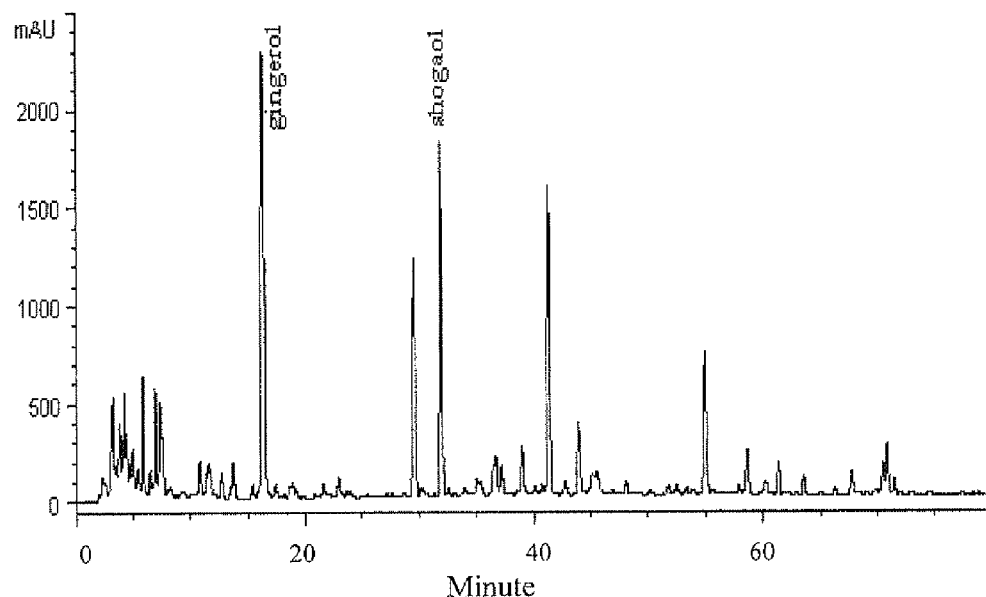
Figure 8:
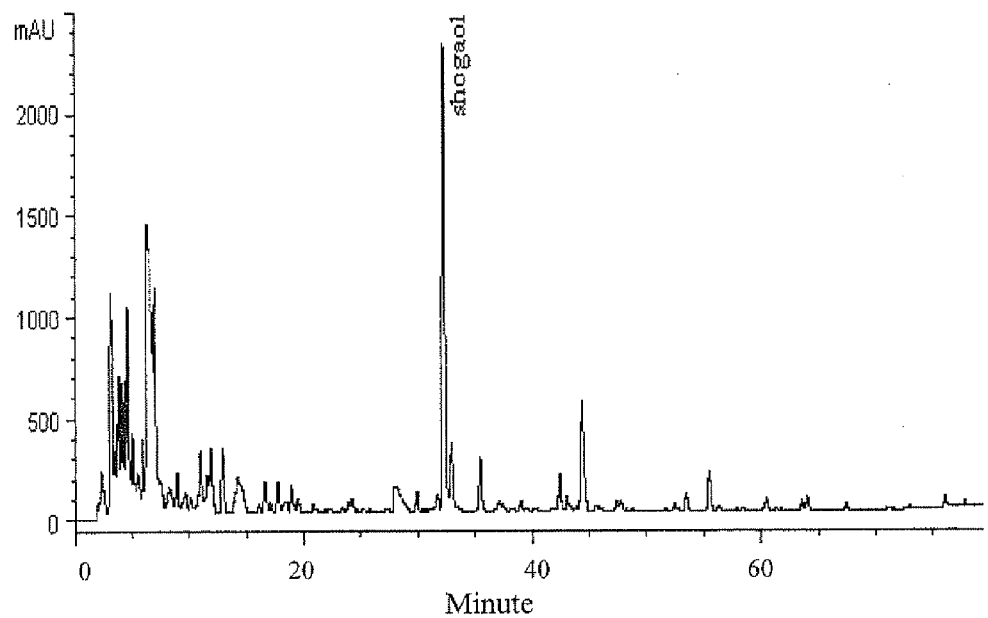
Figure 9:
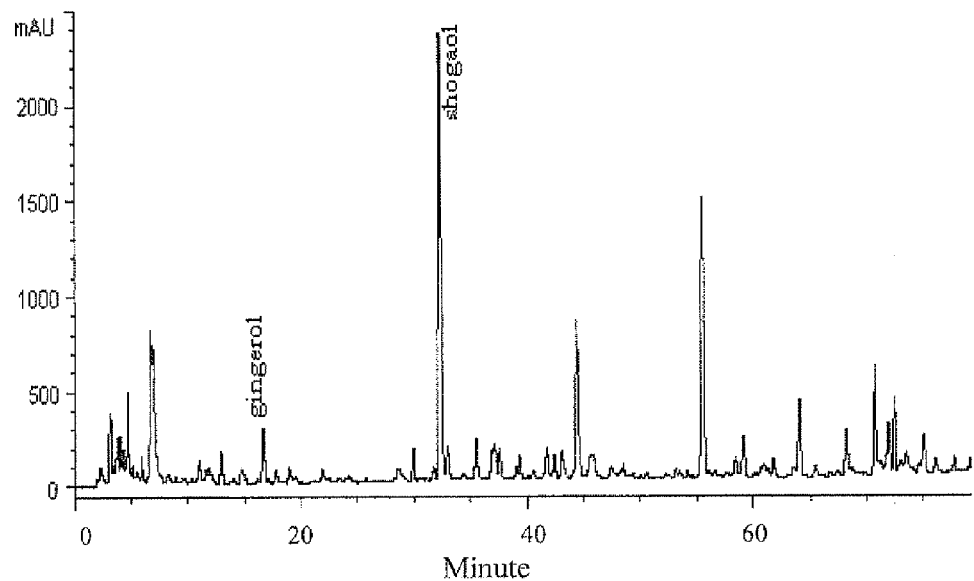

The applicant of this application in GB 2366565 discloses a method of preparing an extract from Zingiber officinale, which is potent in anti-inflammation, anti-platelet aggregation and anti-fungal activity, includes the following steps: preparing a crude liquid from rhizomes of ginger by extraction with an organic solvent or supercritical $CO_2$ or by distillation with steam; introducing the crude liquid to a reverse phase chromatography column, and eluting the column with water, a first eluent and a second eluent having a polarity lower than that of the first eluent but higher than that of chloroform, so that a first eluate resulting from elution of the first eluent and a second eluate resulting from elution of the second eluent are obtained; removing the first eluent and the second eluent from the first eluate and the second eluate by evaporation, respectively, so that a first concentrated eluate and a second concentrated eluate are obtained as the potent extract. The details disclosed in GB 2366565 are incorporated herein by reference.

The invention is further described by means of example, but not in any limitative sense.

Percentages and other amounts referred to in this specification are by weight unless indicated otherwise. Percentages are selected from any ranges used to total 100%.

Example 1

Sliced shade dried rhizomes of ginger were pulverized and screened with a sieve of mesh No. 10. One part by weight of the resulting powder was mixed with 8 parts by weigh of 95% ethanol, and the resulting mixture was boiled under refluxing for one hour and filtered to obtain a filtrate A and a residue. The residue was mixed with 95% ethanol in a weight ratio of 1:8, and the resulting mixture was boiled under refluxing for one hour and filtered to obtain a filtrate B. The filtrate A and filtrate B were combined, and it was concentrated in a water bath of 70° C. and in vacuo (Rotavapor R-220, BÜCHI, Switzerland) by evaporating the solvent therefrom. The resulting concentrate was introduced to a reverse phase chromatography column (7.1 cm×90 cm) packed with Diaion® HP-20 resin (Mitsubishi, Japan) in an amount of 20 times by dry weight of the concentrate of the combined filtrate, which was then eluted with 5 bed volumes of water, 4 bed volumes of 40% ethanol and 4 bed volumes of acetone in sequence. The eluate from the elution of 40% ethanol, and the eluate from the elution of acetone were collected separately. The eluate from 40% ethanol was concentrated in vacuo (Rotavapor R-220, BÜCHI, Switzerland) to dry, and then concentrated again in a water bath of 80° C. and in vacuo (40 mbar) for one hour to obtain Sample 1. The eluate from acetone was concentrated in vacuo (Rotavapor R-220, BÜCHI, Switzerland) to dry, and then concentrated again in a water bath of 80° C. and in vacuo (40 mbar) for one hour to obtain Sample 2.

Example 2

The procedures of Example 1 were repeated except that the eluent of 40% ethanol was replaced by 70% ethanol. Sample 3 was obtained from the elution of 70% ethanol, and Sample 4 was obtained from the elution of acetone.

Example 3

The procedures of Example 1 were repeated to obtain Sample 5, except that the eluent of 40% ethanol was replaced by 95% ethanol.

Example 4

Sliced shade dried rhizomes of ginger were pulverized and screened with a sieve of mesh No. 10. One part by weight of the resulting powder was mixed with 8 parts by weigh of 95% ethanol, and the resulting mixture was boiled under refluxing for one hour and filtered to obtain a filtrate A and a residue. The residue was mixed with 95% ethanol in a weight ratio of 1:8, and the resulting mixture was boiled under refluxing for one hour and filtered to obtain a filtrate B. The filtrate A and filtrate B were combined, and it was concentrated in a water bath of 70° C. and in vacuo (Rotavapor R-220, BÜCHI, Switzerland) to ⅕ of its original weight by evaporating the solvent therefrom. To the resulting concentrate 4 times by weight of water was added to resume its original weight, and the resulting liquid was introduced to a reverse phase chromatography column (7.1 cm×90 cm) packed with Diaion® HP-20 resin (Mitsubishi, Japan) in an amount of 20 times by dry weight of the concentrate of the combined filtrate, which was then eluted with 1 bed volume of 20% ethanol and 4 bed volumes of 70% ethanol in sequence. The eluate from the elution of 70% ethanol was collected and concentrated in vacuo (Rotavapor R-220, BÜCHI, Switzerland) to dry, and then concentrated again in a water bath of 80° C. and in vacuo (40 mbar) for one hour to obtain Sample 6.

Example 5

The procedures of Example 4 were repeated to obtain Sample 7, except that the eluent of 70% ethanol was replaced by 95% ethanol.

Example 6

Sliced shade dried rhizomes of ginger were pulverized and screened with a sieve of mesh No. 10. One part by weight of the resulting powder was mixed with 8 parts by weigh of 95% ethanol, and the resulting mixture was stirred in a homogenizer at 2000 rpm (Type X 50/10, Ystral, Germany) for one hour and filtered to obtain a filtrate A and a residue. The residue was mixed with 95% ethanol in a weight ratio of 1:8, and the resulting mixture was stirred in a homogenizer at 2000 rpm for one hour and filtered to obtain a filtrate B. The filtrate A and filtrate B were combined, and it was concentrated in a water bath of 70° C. and in vacuo (Rotavapor R-220, BÜCHI, Switzerland) to ⅕ of its original weight by evaporating the solvent therefrom. To the resulting concentrate 4 times by weight of water was added to resume its original weight, and the resulting liquid was introduced to a reverse phase chromatography column (7.1 cm×90 cm) packed with Diaion® HP-20 resin (Mitsubishi, Japan) in an amount of 20 times by dry weight of the concentrate of the combined filtrate, which was then eluted with 1 bed volume of 20% ethanol and 4 bed volumes of 70% ethanol in sequence. The eluate from the elution of 70% ethanol was collected and concentrated in vacuo (Rotavapor R-220, BÜCHI, Switzerland) to dry, and then concentrated again in a water bath of 80° C. and in vacuo (40 mbar) for one hour to obtain Sample 8.

Example 7

The procedures of Example 6 were repeated to obtain Sample 9, except that the eluent of 70% ethanol was replaced by 95% ethanol.

Example 8

Sliced shade dried rhizomes of ginger were pulverized and screened with a sieve of mesh No. 10. One part by weight of the resulting powder was mixed with 8 parts by weigh of acetone, and the resulting mixture was boiled under refluxing for one hour and filtered to obtain a filtrate A and a residue. The residue was mixed with acetone in a weight ratio of 1:8, and the resulting mixture was boiled under refluxing for one hour and filtered to obtain a filtrate B. The filtrate A and filtrate B were combined, and it was concentrated in a water bath of 70° C. and in vacuo (Rotavapor R-220, BÜCHI, Switzerland) by evaporating the solvent therefrom. The resulting concentrate was introduced to a reverse phase chromatography column (7.1 cm×90 cm) packed with Diaion® HP-20 resin (Mitsubishi, Japan) in an amount of 20 times by dry weight of the concentrate of the combined filtrate, which was then eluted with 5 bed volumes of water, 4 bed volumes of 40% ethanol and 2 bed volumes of acetone in sequence. The eluate from the elution of acetone were collected and concentrated in vacuo (Rotavapor R-220, BÜCHI, Switzerland) to dry, and then concentrated again in a water bath of 80° C. and in vacuo (40 mbar) for one hour to obtain Sample 10.

Example 9

The procedures of Example 8 were repeated to obtain Sample 11, except that the eluent of 40% ethanol was replaced by 70% ethanol. The eluate from the elution of 70% ethanol were collected and concentrated in vacuo (Rotavapor R-220, BÜCHI, Switzerland) to dry, and then concentrated again in a water bath of 80° C. and in vacuo (40 mbar) for one hour to obtain Sample 11.

Example 10

The procedures of Example 8 were repeated to obtain Sample 12, except that the powder and the residue were boiled with ethyl acetate instead of acetone.

Example 11

The procedures of Example 9 were repeated to obtain Sample 13, except that the powder and the residue were boiled with ethyl acetate instead of acetone.

Example 12

Sliced shade dried rhizomes of ginger were pulverized and screened with a sieve of mesh No. 10. One part by weight of the resulting powder was mixed with 8 parts by weight of 95% ethanol, and the resulting mixture was boiled under refluxing for one hour and filtered to obtain a filtrate A and a residue. The residue was mixed with 95% ethanol in a weight ratio of 1:8, and the resulting mixture was boiled under refluxing for one hour and filtered to obtain a filtrate B. The filtrate A and filtrate B were combined, and it was concentrated in a water bath of 70° C. and in vacuo (Rotavapor R-220, BÜCHI, Switzerland) by evaporating the solvent therefrom. The resulting concentrate was introduced to a normal phase chromatography column packed with 20 times by weight of silica gel 60 (Merck, Germany), which was then eluted with 4 bed volumes of a mixed eluent of n-hexane:ethyl acetate=9:1, 3 bed volumes of a mixed eluent of n-hexane:ethyl acetate=6:4 and 2 bed volumes of a mixed eluent of ethyl acetate:methanol=1:1 in sequence. The eluate from the elution of n-hexane:ethyl acetate=9:1 was collected and concentrated in vacuo (Rotavapor R-220, BÜCHI, Switzerland) to dry, and then concentrated again in a water bath of 80° C. and in vacuo (40 mbar) for one hour to obtain Sample 14. Samples 15 and 16 were obtained from the elution of n-hexane:ethyl acetate=6:4, and the elution of ethyl acetate:methanol=1:1 respectively by the same procedures as used in obtaining Sample 14.

Example 13

The procedures of Example 12 were repeated except that the 95% ethanol was replaced by acetone. Samples 17, 18 and 19 were obtained from the elution of n-hexane:ethyl acetate=9:1, n-hexane:ethyl acetate=6:4, and ethyl acetate:methanol=1:1 respectively.

Example 14

Sliced shade dried rhizomes of ginger were pulverized and screened with a sieve of mesh No. 10. One part by weight of the resulting powder was mixed with 8 parts by weigh of 95% ethanol, and the resulting mixture was boiled under refluxing for one hour and filtered to obtain a filtrate A and a residue. The residue was mixed with 95% ethanol in a weight ratio of 1:8, and the resulting mixture was boiled under refluxing for one hour and filtered to obtain a filtrate B. The filtrate A and filtrate B were combined, and it was concentrated with a thin-film vacuum evaporator (CEP-L, Okawara Mfg. Co., Japan) to 1/5 of its original weight by evaporating the solvent therefrom. The resulting concentrate was introduced to a reverse phase chromatography column (34.5 cm×100 cm) packed with Diaion® HP-20 resin (Mitsubishi, Japan) in an amount of 20 times by dry weight of the concentrate, which was then eluted with 2 bed volumes of 95% ethanol and 2 bed volumes of acetone in sequence. The eluate from the elution of acetone was collected and concentrated in vacuo (Rotavapor R-220, BÜCHI, Switzerland) to dry, and then concentrated again in a water bath of 80° C. and in vacuo (40 mbar) for one hour to obtain Sample 20.

HPLC Analysis

Sample Preparation:

Accurately weigh sample into a sample bottle and dissolve with methanol to make a sample solution with concentration of 10 mg/ml. Filter the sample solution with 0.45 μm filter and analyze the filtrate with HPLC.

HPLC Condition:

| | | | |
|---|---|---|---|
| Column: Cosmosil 5C18-MS-II 4.6 × 250 mm (Nacalai Tesque Inc.) | | | |
| Guard column: Lichrospher ® 100 RP-18e (5 μm) (Merck) | | | |
| Flow rate: 1 ml/min | | | |
| Sample injection volume: 10 μl | | | |
| Time (min) | 0 | 10 | 80 |
| Acetonitrile (%) | 40 | 40 | 100 |
| 0.1% Phosphoric acid* (%) | 60 | 60 | 0 |
| Column thermostat | | 37° C. | |
| Detector wavelength | | 204 nm | |

*0.1% Phosphoric acid: take $H_3PO_4$ (85% w/v) 2.35 ml and dilute with $H_2O$ to 2000 ml The results of the HPLC analysis of Sample 1 to Sample 20 prepared above are shown in FIG. 1 to FIG. 20. The contents of 6-gingerol and 6-shogaol in the samples (mg/g) were calculated from the HPLC analysis and are listed in Table 1 together with the extraction conditions and elution conditions used in the preparation of the samples.

TABLE 1

| | Content of 6-gingerol in sample (mg/g) | Content of 6-shogaol in sample (mg/g)) | Extraction Conditions | Elution Conditions |
|---|---|---|---|---|
| Sample 1 | — | — | 95% Ethanol refluxing | 1) 40% EtOH after $H_2O$ |
| Sample 2 | 23.11 | 67.20 | 95% Ethanol refluxing | Acetone following 1) |
| Sample 3 | 31.14 | 33.76 | 95% Ethanol refluxing | 2) 70% EtOH after $H_2O$ |
| Sample 4 | — | 68.36 | 95% Ethanol refluxing | Acetone following 2) |
| Sample 5 | 35.36 | 54.32 | 95% Ethanol refluxing | 95% EtOH after $H_2O$ |
| Sample 6 | 23.85 | 85.18 | 95% Ethanol refluxing | 70% EtOH after 20% EtOH |
| Sample 7 | 94.79 | 55.80 | 95% Ethanol refluxing | 95% EtOH after 20% EtOH |
| Sample 8 | — | 84.53 | 95% Ethanol mixing in homogenizer | 70% EtOH after 20% EtOH |

TABLE 1-continued

|  | Content of 6-gingerol in sample (mg/g) | Content of 6-shogaol in sample (mg/g)) | Extraction Conditions | Elution Conditions |
|---|---|---|---|---|
| Sample 9 | 8.98 | 87.15 | 95% Ethanol mixing in homogenizer | 95% EtOH after 20% EtOH |
| Sample 10 | 39.28 | 67.53 | Acetone refluxing | Acetone following (40% EtOH after $H_2O$) |
| Sample 11 | 66.94 | 103.48 | Acetone refluxing | 70% EtOH after $H_2O$ |
| Sample 12 | 38.22 | 66.16 | EA refluxing | Acetone following (40% EtOH after $H_2O$) |
| Sample 13 | 112.97 | 34.37 | " | 70% EtOH after $H_2O$ |
| Sample 14 | — | — | 95% Ethanol refluxing | 3) n-Hexane:EA = 9:1 |
| Sample 15 | 69.48 | 96.95 | 95% Ethanol refluxing | 4) n-Hexane:EA = 6:4 following 3) |
| Sample 16 | — | — | 95% Ethanol refluxing | EA:MeOH = 1:1 following 4) |
| Sample 17 | — | — | Acetone refluxing | 5) n-Hexane:EA = 9:1 |
| Sample 18 | 84.37 | 105.68 | Acetone refluxing | 6) n-Hexane:EA = 6:4 following 5) |
| Sample 19 | — | — | Acetone refluxing | EA:MeOH = 1:1 following 6) |
| Sample 20 | — | — | 95% Ethanol refluxing | Acetone following 95% EtOH |

Figure 10:
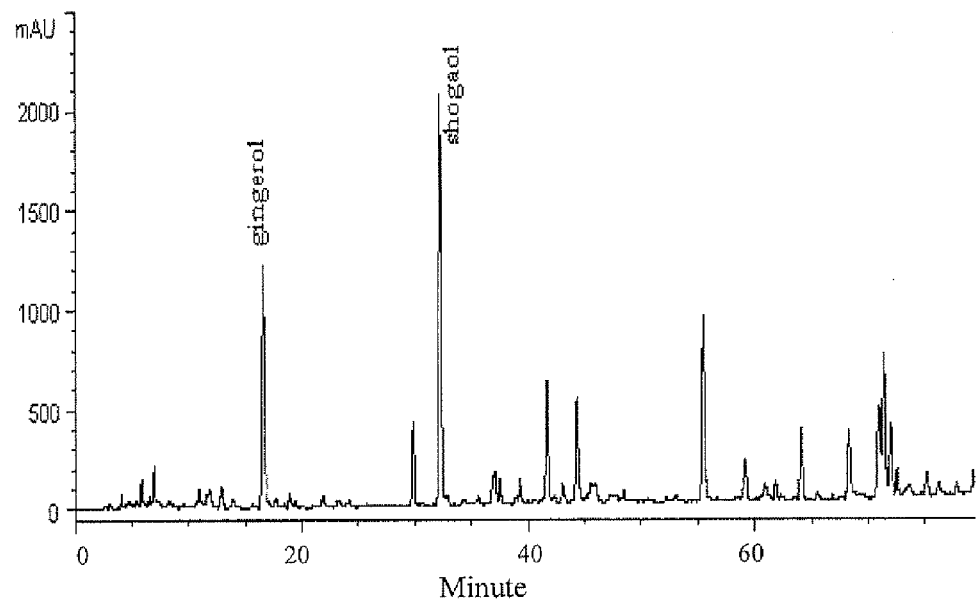
Figure 11:
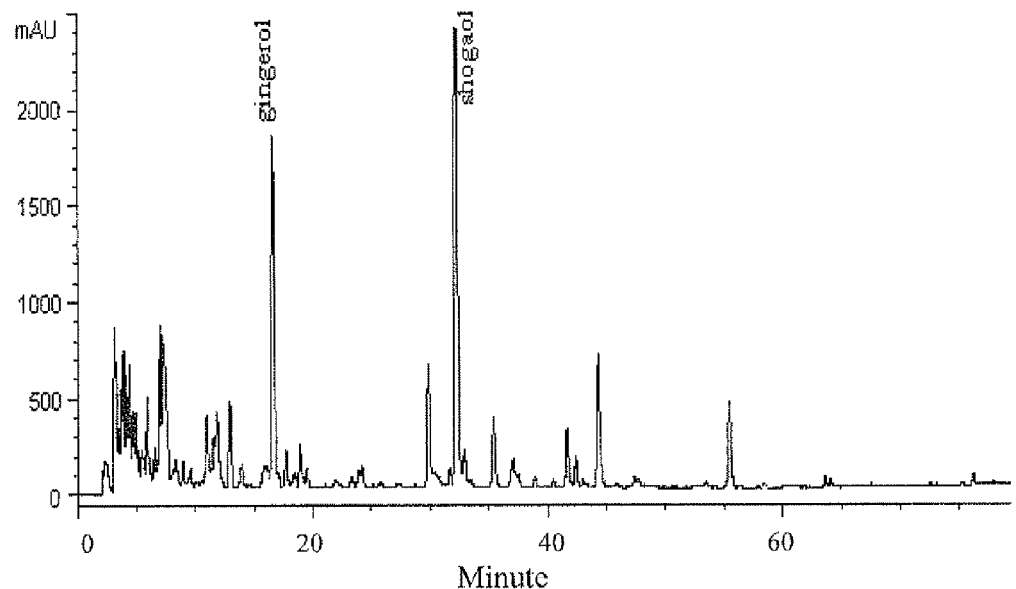
Figure 12:
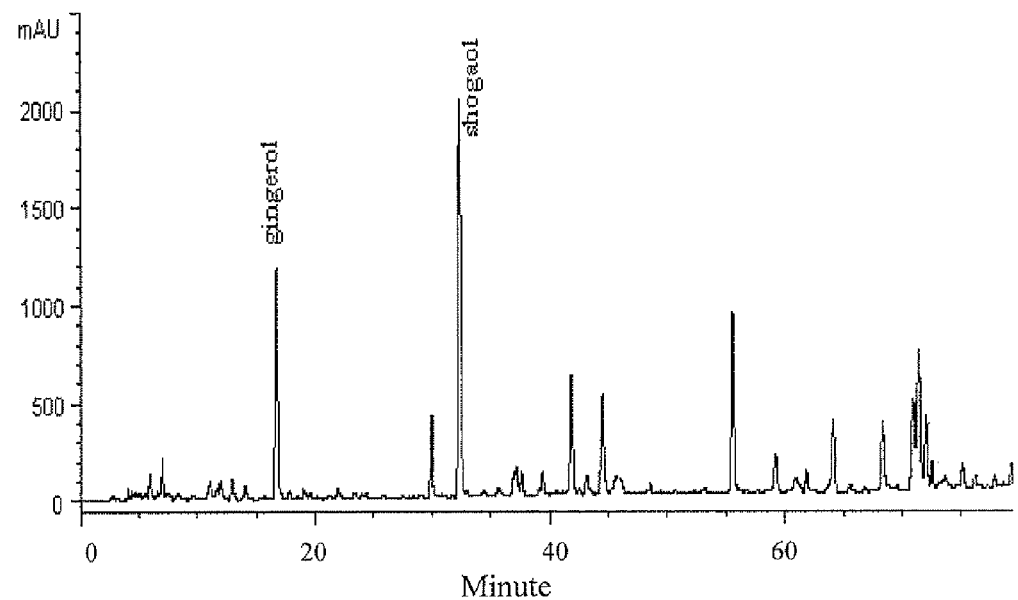
Figure 13:
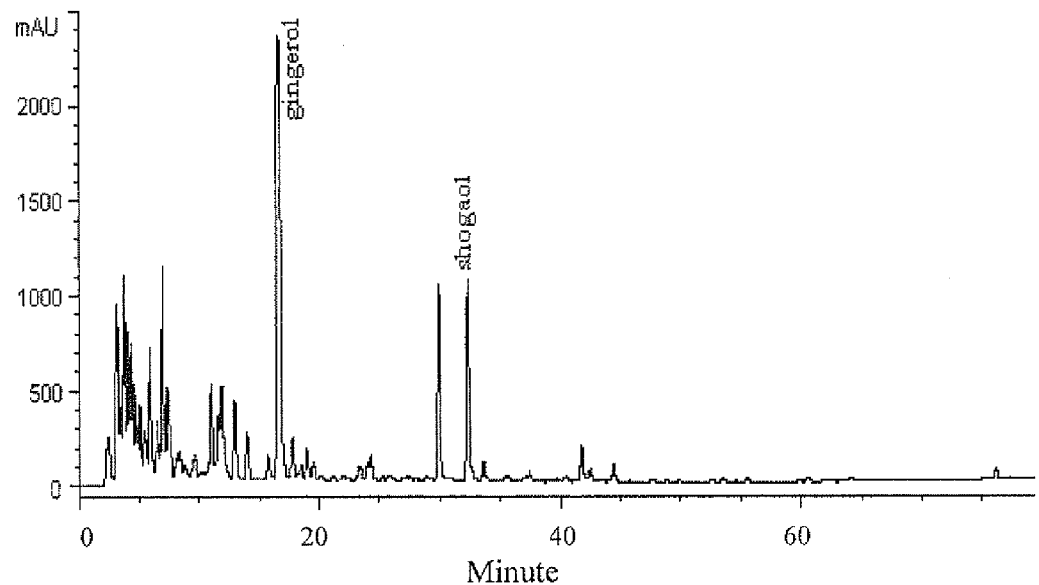
Figure 14:
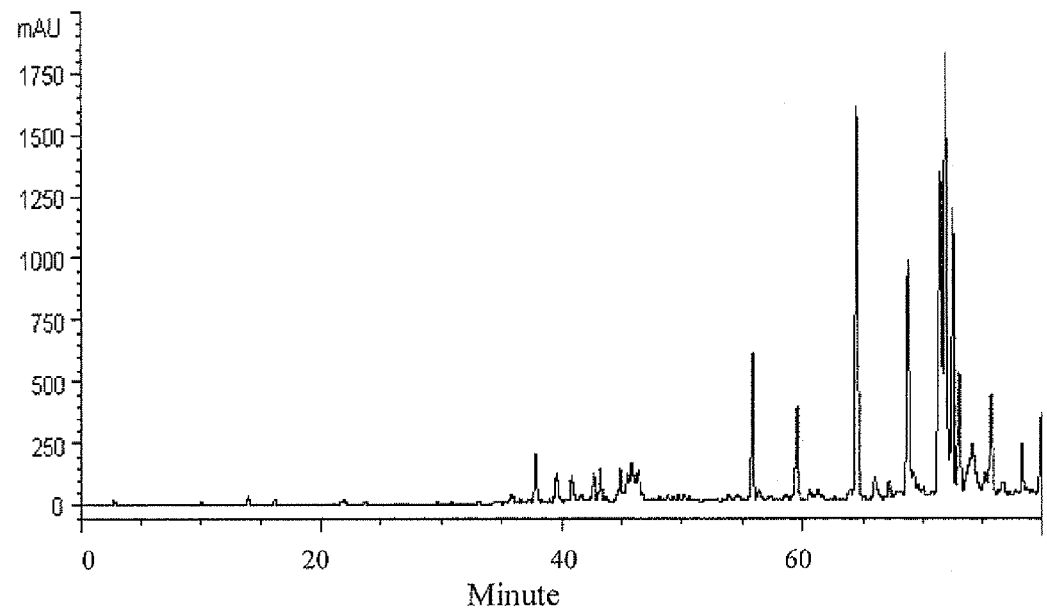
Figure 15:
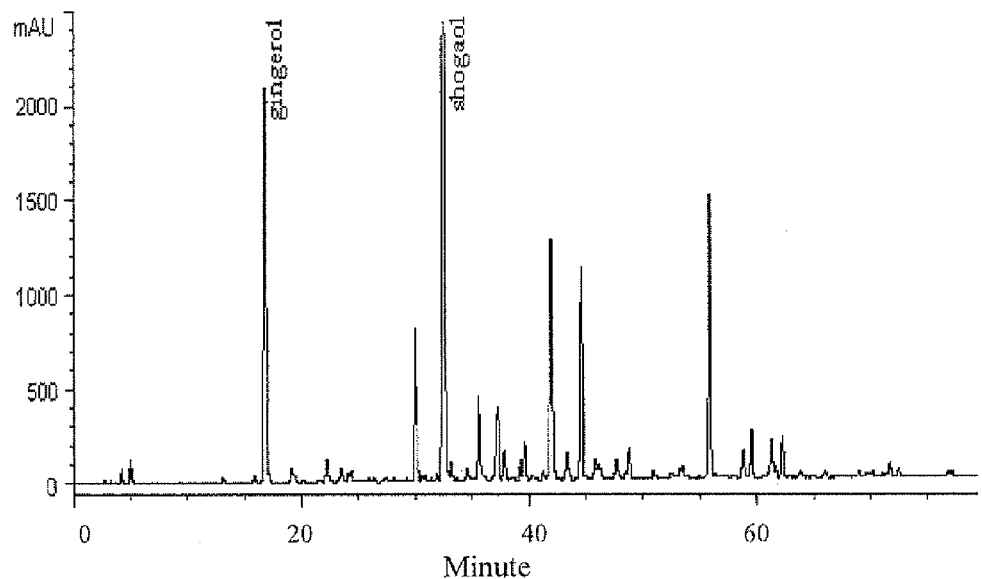
Figure 16:
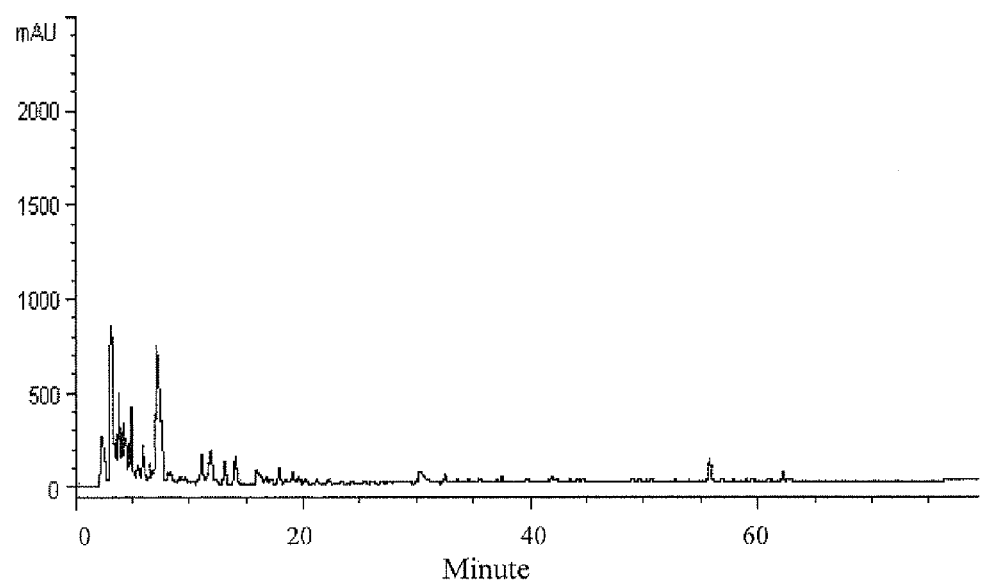
Figure 17:
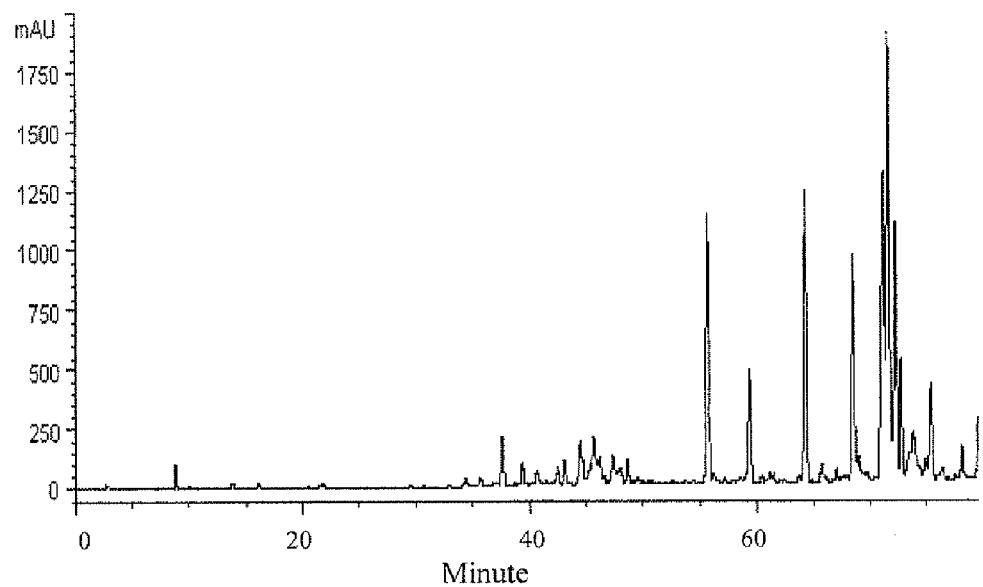
Figure 18:
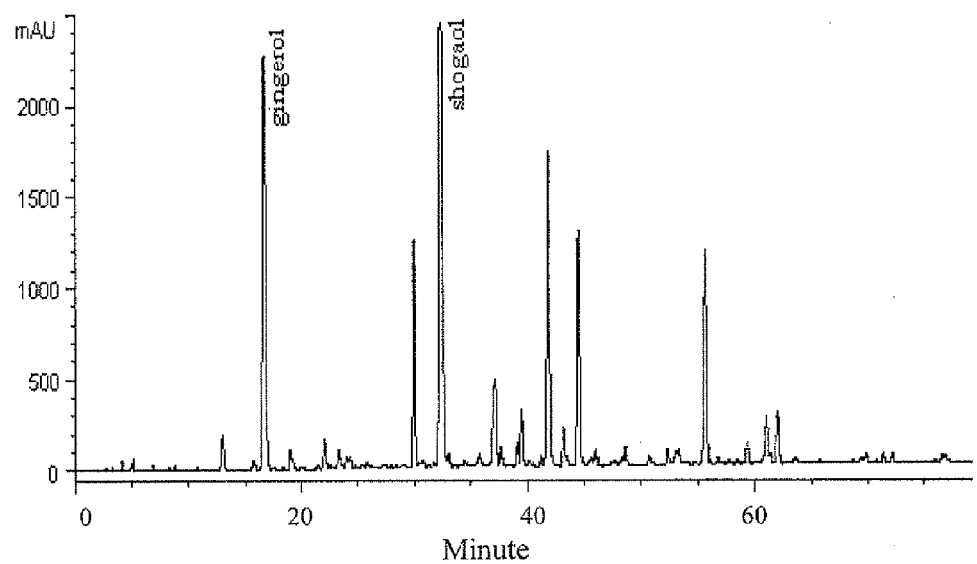
Figure 19:
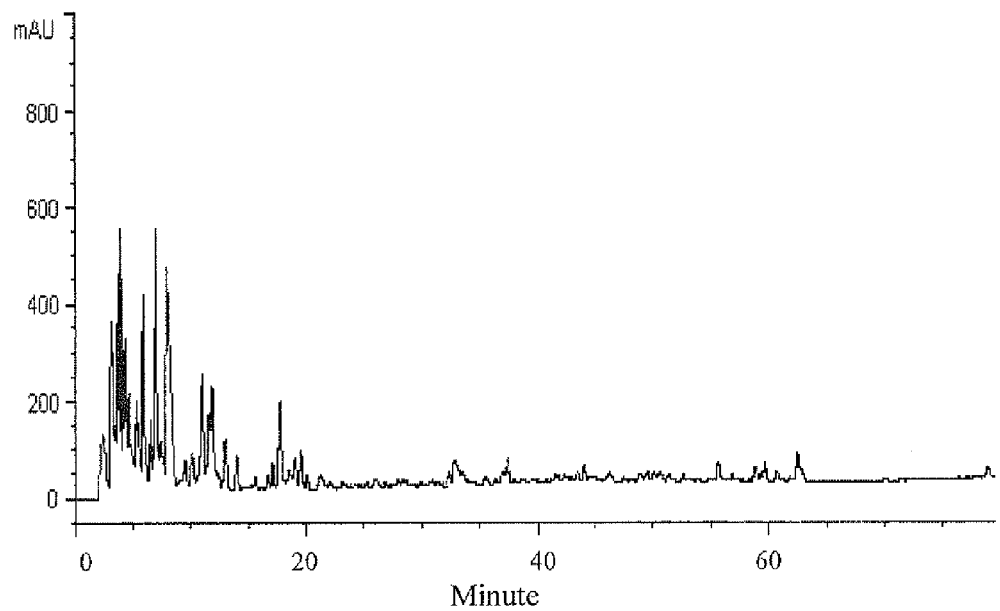
Figure 20:
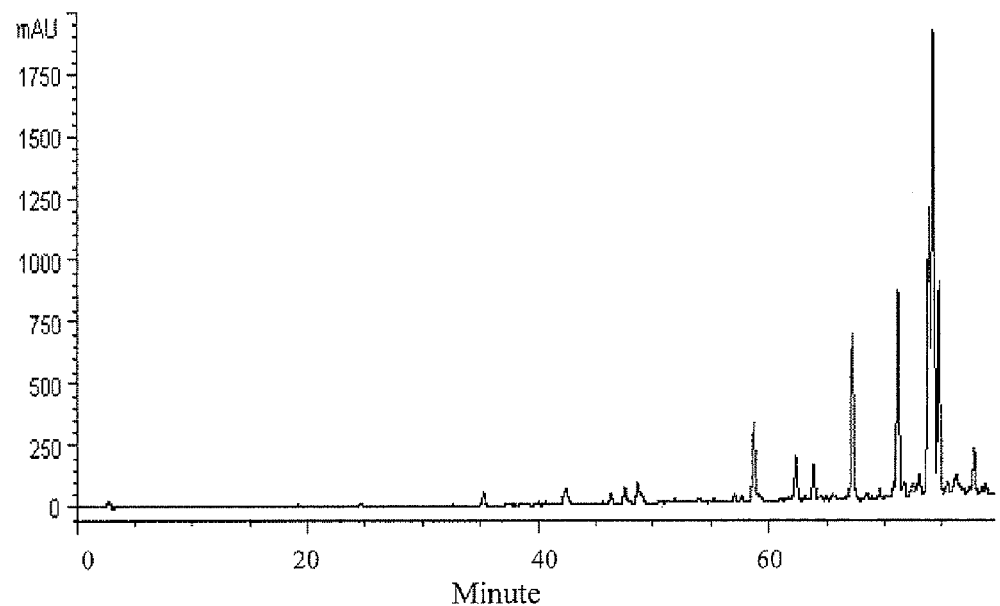

"—": indicates that there is no detectable 6-gingerol or 6-shogaol in the sample Samples 1 to 13 and 20 were prepared by using the reverse phase chromatography column. In comparison with the HPLC analysis fingerprints shown in FIGS. 1 to 4 it can be seen that the eluate from the elution of 40% ethanol contains compounds which are more polar than 6-gingerol (Sample 1), the eluate from the elution of 70% ethanol contains compounds which are more polar than 6-gingerol, and 6-gingerol and 6-shogaol (Sample 3), and the eluate from the elution of acetone contains the remaining relatively less polar compounds (Sample 2 and Sample 4). It can be seen from FIG. 6 and FIG. 7 that more peaks can be seen in the right side when 95% ethanol is used as the eluent in contrast to 70% ethanol. Same trend can be observed in FIGS. 8 and 9 as in FIGS. 6 and 7, where the extraction conditions are different. The fingerprints shown in FIGS. 10 and 12 are similar to those shown in FIG. 2, where the extraction conditions are different but the elution conditions are the same. The fingerprints shown in FIGS. 11 and 13 are similar to those shown in FIG. 3, where the extraction conditions are different but the elution conditions are the same. Sample 20 contains mostly the less polar compounds and no detectable 6-gingerol and 6-shogaol as shown in FIG. 20, which indicates that 95% ethanol eluent has eluted most of the relatively more polar compounds including 6-gingerol and 6-shogaol from the reverse phase chromatography column. Samples 13 to 15 are similar to Samples 16 to 19 in the HPLC analysis (FIGS. 13 to 19), where the extraction conditions are different but the elution conditions to the normal phase chromatography column are the same. Sample 14 (Sample 16) contains mostly the nonpolar compounds and no detectable amount of 6-gingerol and 6-shogaol as shown in FIG. 14 (FIG. 16) by using the eluent of n-hexane:ethyl acetate=9:1, and Sample 15 (Sample 17) contains significant amounts of 6-gingerol and 6-shogaol by using the eluent of n-hexane:ethyl acetate=6:4.

1. Anti-microbial Test

Minimum inhibitory concentration (MIC) of sample on *Helicobacter pylori* was determined by the agar dilution method [Malanosk G. J. et al. Effect of pH variation on the susceptibility of *Helicobacter pylori* to three marcolide antimicrobial agents and temafloxacin. Eur. J. Clin. Microbial Infect Dis. 12: pp. 131-133, 1993.]. The test substance was dissolved and serially diluted in DMSO to desired stock concentrations. For each concentration tested, a 0.01 ml aliquot is added to a 48-well plate containing 0.99 ml of Columbia agar base (Oxoid, England) supplemented 7% defibrinated rabbit blood. The inoculum of *Helicobacter pylori* (ATCC 43504) is prepared by suspending in brain heart infusion broth to a density of $5 \times 10^5$ CFU/ml. The final maximal concentration of DMSO is 1% and the initial test substance concentration is 300 μg/ml. The plates are incubated at 35° C. for 72 hours in the microaerophilic condition (Mixed gas $N_2$ 85%, $CO_2$ 10% and $O_2$ 5%) and then visually examined and scored positive (+) for inhibition of the colonies growth or negative (−) for no effect upon growth colonies. Vehicle-control and gentamicin are used as blank and positive controls, respectively. Each concentration is evaluated in duplicate. The results are shown in Table 2.

TABLE 2

| Samples | Minimum inhibitory concentration (MIC, μg/ml) |
|---|---|
| Sample 1 | —* |
| Sample 2 | 30 |
| Sample 3 | 30 |
| Sample 4 | 30 |
| Sample 5 | —* |
| Sample 6 | 30 |
| Sample 7 | 30 |
| Sample 8 | 30 |
| Sample 9 | 30 |
| Sample 10 | 30 |
| Sample 11 | 30 |
| Sample 12 | 100 |
| Sample 13 | 10 |
| Sample 14 | 30 |
| Sample 15 | 10 |
| Sample 16 | 30 |
| Sample 17 | 30 |

TABLE 2-continued

| Samples | Minimum inhibitory concentration (MIC, μg/ml) |
|---|---|
| Sample 18 | 10 |
| Sample 19 | 300 |
| Sample 20 | 10 |
| Gingerol | 10 |
| Shogaol | 10 |

*Minimum inhibitory concentrations (MIC) of Sample 1 and Sample 5 on *Helicobacter pylori* are higher than 300 μg/ml.

2. *Helicobacter pylori*-Induced Gastric Ulcer

Effects of samples on *Helicobacter pylori*-induced gastric ulcer were evaluated as described previously [Marchetti, M., Arico, B., Burroni, D., Figura, N., Rappuoli, R. and Ghiara, P. Development of a mouse model of *Helicobacter pylori* infection that mimics human disease. Science 267: 1655-1658, 1995.]. Groups of 5 male CD-1 (Crl.) derived mice weighing 24±2 g were fasted for 18 hours prior to intragastric inoculation of clinical isolated *Helicobacter pylori* in suspension at $3.2 \times 10^9$ colony formation units/0.4 ml/mouse. Test samples and vehicle (2% CMC, 10 ml/kg) were each administered orally to test animals, starting one hour after the *Helicobacter pylori* inoculation, dosing twice daily (10:00 am and 4:00 pm) for 7 consecutive days. Omeprazole (1 mg/kg) and clarithromycin (10 mg/kg), in combination, were used for the positive control agents and administered orally to test animal once daily for 7 consecutive days under the same schedule. Eight days after infection, all animals were fasted overnight, sacrificed and stomachs dissected along the greater curvature. Gastric ulceration scored at four levels according to the degree of hemorrhage and severity of ulcerative lesions:
0=normal appearance
1=mild red spots
2=moderate red spots and/or hemorrhage spots
3=marked hemorrhage spots Percentage inhibition on *Helicobacter pylori*-induced gastric ulcer was calculated as follows:

(Scores of vehicle group−Scores of test group)/
(Scores of vehicle group)×100%

The results are shown in Table 3.

TABLE 3

| Samples | Dose | Percentage inhibition on *Helicobacter pylori* - induced gastric ulcer |
|---|---|---|
| Vehicle | 10 ml/kg | 0 |
| Sample 1 | 300 mg/kg | 17 |
| Sample 2 | 300 mg/kg | 66 |
| Sample 3 | 300 mg/kg | 83 |
| Sample 4 | 300 mg/kg | 73 |
| Sample 5 | 300 mg/kg | 50 |
| Sample 6 | 300 mg/kg | 64 |
| Sample 7 | 300 mg/kg | 71 |
|  | 100 mg/kg | 57 |
| Sample 8 | 300 mg/kg | 57 |
| Sample 9 | 300 mg/kg | 57 |
| Sample 10 | 300 mg/kg | 47 |
| Sample 11 | 300 mg/kg | 73 |
| Sample 12 | 300 mg/kg | 67 |
| Sample 13 | 300 mg/kg | 73 |
| Sample 14 | 300 mg/kg | 58 |
| Sample 15 | 300 mg/kg | 67 |
| Sample 16 | 300 mg/kg | 58 |
| Sample 17 | 300 mg/kg | 58 |
| Sample 18 | 300 mg/kg | 75 |
| Sample 19 | 300 mg/kg | 65 |
| Sample 20 | 100 mg/kg | 83 |
|  | 30 mg/kg | 75 |
|  | 10 mg/kg | 67 |
|  | 3 mg/kg | 50 |

TABLE 3-continued

| Samples | Dose | Percentage inhibition on *Helicobacter pylori* - induced gastric ulcer |
|---|---|---|
| 6-Gingerol | 35 mg/kg | 25 |
| Omeprazole and Clarithromycin | 1 mg/kg + 10 mg/kg | 83 |

Only Sample 1 is less effective than 6-gingerol in treating gastric ulcer induced by *Helicobacter pylori* among the samples prepared in the above examples. Sample 20 is the most effective, which has 83%, 75%, 67% and 50% inhibition on *Helicobacter pylori*-induced gastric ulcer at dosages of 100 mg/kg, 30 mg/kg, 10 mg/kg and 3 mg/kg, respectively.

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

The invention claimed is:

1. A method of treating a disease associated with *Helicobacter pylori* in a patient comprising inhibiting the growth of *Helicobacter pylori* in the stomach of the patient by administering to the patient a therapeutically effective amount of a product prepared from rhizomes of *Zingiber officinale*, said product being prepared by a process comprising the following steps:
    a) preparing a crude extract from rhizomes of *Zingiber officinale*, said crude extract comprising 6-gingerol and 6-shogaol;
    b) introducing the crude extract to a normal phase chromatography column, and eluting the column with a first eluent, said first eluent having a polarity lower than that of a mixture of n-hexane and ethyl acetate in a weight ratio of 6:4, so that a first eluate resulting from elution of the first eluent is obtained; and
    c) removing the first eluent from the first eluate by evaporation, so that a first concentrated eluate is obtained and is used as the product;
    wherein step a) comprises steps i) to iv), or comprises step I), step I'), or step I"), wherein said steps i) to iv) are:
    i) shedding fresh rhizomes of *Zingiber officinale* and filtering the resulting mixture to obtain a filtrate and a residue;
    ii) extracting the filtrate with a first organic solvent, recovering the resulting extraction solution of the first organic solvent, and evaporating the first organic solvent from the extraction solution to obtain a first concentrated extraction solution;
    iii) extracting the residue with a second organic solvent, recovering the resulting extraction solution of the second organic solvent, and evaporating the second organic solvent from the extraction solution to obtain a second concentrated extraction solution; and
    iv) combining the first concentrated extraction solution and the second concentrated extraction solution to obtain the crude extract;
    said step I) is:
    I) extracting dried rhizomes of *Zingiber officinale* with an organic solvent, recovering the resulting extraction solution of the organic solvent, and evaporating the organic solvent from the extraction solution to obtain the crude extract;

said step I') is:

I') steam distilling dried rhizomes of *Zingiber officinale*, and concentrating the resulting distillate by evaporation to obtain the crude extract; and said step I") is:

I") extracting powder of dried rhizomes of *Zingiber officinale* with supercritical $CO_2$, recovering the resulting extraction solution of the supercritical $CO_2$, and evaporating $CO_2$ from the extraction solution to obtain the crude extract, and wherein said first concentrated eluate is free of both 6-gingerol and 6-shogaol.

2. The method according to claim 1, wherein said disease is gastric ulcer.

3. The method according to claim 1, wherein said crude extract is prepared from the method comprising step i) to iv).

4. The method according to claim 3, wherein said first organic solvent is ethyl ether, and said second organic solvent is acetone, methanol, ethanol, a mixture of methanol and water, a mixture of ethanol and water, or a combination of them.

5. The method according to claim 4, wherein said second organic solvent is acetone.

6. The method according to claim 1, wherein said crude extract is prepared from the method comprising step I).

7. The method according to claim 6, wherein said organic solvent is acetone, methanol, ethanol, a mixture of methanol and water, a mixture of ethanol and water, or a combination of them.

8. The method according to claim 7, wherein said organic solvent is acetone, ethanol or a mixture of ethanol and water.

9. The method according to claim 1, wherein the first eluent has the polarity of a mixture of n-hexane and ethyl acetate in a weight ratio of 9:1.

10. The method according to claim 9, wherein the first eluent is a mixture of n-hexane and ethyl acetate in a weight ratio of 9:1.

11. A method of inhibiting the growth of *Helicobacter pylori* in the stomach of a patient comprising administering to the patient a therapeutically effective amount of a product prepared from rhizomes of *Zingiber officinals*, said product being prepared by a process comprising the following steps:

a) preparing a crude extract from rhizomes of *Zingiber officinale*, said crude extract comprising 6-gingerol and 6-shogaol;

b) introducing the crude extract to a normal phase chromatography column, and eluting the column with a first eluent, said first eluent having a polarity lower than that of a mixture of n-hexane and ethyl acetate in a weight ratio of 6:4, so that a first eluate resulting from elution of the first eluent is obtained; and c) removing the first eluent from the first eluate by evaporation, so that a first concentrated eluate is obtained and is used as the product;

wherein step a) comprises steps i) to iv), or comprises step I), step I'), or step I"), wherein said steps i) to iv) are:

i) shedding fresh rhizomes of *Zingiber officinale* and filtering the resulting mixture to obtain a filtrate and a residue;

ii) extracting the filtrate with a first organic solvent, recovering the resulting extraction solution of the first organic solvent, and evaporating the first organic solvent from the extraction solution to obtain a first concentrated extraction solution;

iii) extracting the residue with a second organic solvent, recovering the resulting extraction solution of the second organic solvent, and evaporating the second organic solvent from the extraction solution to obtain a second concentrated extraction solution; and iv) combining the first concentrated extraction solution and the second concentrated extraction solution to obtain the crude extract;

said step I) is:

I) extracting dried rhizomes of *Zingiber officinale* with an organic solvent, recovering the resulting extraction solution of the organic solvent, and evaporating the organic solvent from the extraction solution to obtain the crude extract;

said step I') is:

I') steam distilling dried rhizomes of *Zingiber officinale*, and concentrating the resulting distillate by evaporation to obtain the crude extract; and said step I") is:

I") extracting powder of dried rhizomes of *Zingiber officinale* with supercritical $CO_2$, recovering the resulting extraction solution of the supercritical $CO_2$, and evaporating $CO_2$ from the extraction solution to obtain the crude extract, and wherein said first concentrated eluate is free of both 6-gingerol and 6-shogaol.

* * * * *